United States Patent [19]
Cleveland et al.

[11] Patent Number: 6,048,901
[45] Date of Patent: Apr. 11, 2000

[54] METHOD OF REDUCING INTESTINAL GAS, CRAMPING AND ANORECTAL IRRITATION

[75] Inventors: Mark vB. Cleveland; Russell W. Pelham, both of Duxbury, Mass.

[73] Assignee: Braintree Laboratories, Inc., Braintree, Mass.

[21] Appl. No.: 09/348,376

[22] Filed: Jul. 7, 1999

Related U.S. Application Data

[60] Provisional application No. 60/130,115, Apr. 20, 1999.
[51] Int. Cl.⁷ ..................................................... A61K 31/08
[52] U.S. Cl. ............................................................ 514/723
[58] Field of Search ............................................. 514/723

[56] References Cited

U.S. PATENT DOCUMENTS 5,710,183  1/1998  Halow ...................................... 514/892

OTHER PUBLICATIONS

Andorsky et al., Am. J. Gastroent. 85:261 (1990).

Attar et al., Gutt 44:226 (1999).

*Primary Examiner*—Phyllis Spivack
*Attorney, Agent, or Firm*—Cesari and McKenna, LLP

[57] ABSTRACT

Intestinal gas, cramping and/or anorectal irritation are treated by oral administration of an effective or sufficient amount of a composition comprising polyethylene glycol, preferably dispersed and/or dissolved in an aqueous medium. The PEG compositions used for the present invention are desirably substantially free of ancillary electrolytes.

13 Claims, No Drawings

METHOD OF REDUCING INTESTINAL GAS, CRAMPING AND ANORECTAL IRRITATION

PRIOR APPLICATION

This application stems from provisional application U.S. Ser. No. 60/130,115, filed Apr. 20, 1999.

FIELD OF THE INVENTION

The present invention relates to amelioration of intestinal cramping and gas.

BACKGROUND OF THE INVENTION

Excess flatus or intestinal gas represents an intestinal disorder that contributes to the condition known as gastrointestinal distress. Intestinal gas exists as trapped bubbles that cause feelings of pain, bloating and cramping in the abdominal area. These symptoms frequently accompany constipation, the most common gastrointestinal complaint in the United States. In addition, constipation is frequently associated with anorectal irritation due to the difficulty of passing dry, hard stool. Over 4,000,000 people (approximately 2% of the population) have frequent constipation as determined by self-assessment surveys.

Unfortunately, intestinal gas and cramping tend to be exacerbated by standard treatments for constipation (such as the use of laxatives or increasing oral intake of fiber). Indeed, constipation remedies frequently warn consumers that cramping and gas may accompany their use.

DESCRIPTION OF THE INVENTION

It has been determined, surprisingly, that a compound—polyethylene glycol, or PEG—known for treatment of constipation can also be used to reduce symptoms of intestinal gas and cramping. This finding is highly unexpected not only in that treatment of constipation generally worsens, rather than ameliorates gas and cramping, but more specifically in light of studies indicating that PEG compositions, used as laxatives, actually increase (or at best do not exacerbate) these conditions. See Andorsky et al., *Am. J. Gastroent.* 85:261 (1990); Attar et al., *Gut* 44:226 (1999); Lémann et al., *Gastroenterology* 1 10:A704 (1996). It has also been determined that PEG is useful in reducing anorectal irritation.

Therefore, in accordance with the invention, intestinal gas, cramping and/or anorectal irritation are treated by oral administration of an effective or sufficient amount of a composition comprising PEG. Preferably, PEG compositions used for the present invention are substantially free of ancillary electrolytes; by "substantially free" is meant containing less than 1% by weight, and desirably as close to 0% as practicable. This is because salts may exert a constipative effect, thereby indirectly exacerbating gas-related intestinal discomfort. In particular, low doses of salt cross the intestinal mucosa and, due to solvent drag, withdraw water from the intestinal contents, which can increase or induce constipation.

Any food- or pharmaceutical-grade PEG polymer may be employed in the compositions contemplated herein. Polymers of relatively high molecular weight (e.g., above about 900) that are solid at room temperature (i.e., about 25° C.) and soluble in (or miscible with) water at room temperature are currently preferred. Polymers having an average molecular weight of at least 1000 (and generally no greater than 20,000) are exemplary, while an average molecular weight between about 3000 and 8000 is preferred; and PEG 3350 (the numeric designation identifying the average molecular weight) is especially preferred.

Compositions according to the invention are prepared by dispersing and/or dissolving the PEG in water or other aqueous medium to formulate a relatively smooth, palatable drink. PEG is an osmotically active agent that is not significantly absorbed in the gut, and may therefore be taken in dosages ranging from about 5 to about 200 g up to four times per day. Preferably, anywhere from 10 to 30 g (depending on symptom severity) of PEG in solid form are conveniently dispersed/dissolved in from about 6 to about 10 fl. oz. (i.e., about 10–12 times the weight of the solid PEG) of water, and the mixture ingested orally up to four times per day as necessary for relief of symptoms. PEG may be furnished in solid form for dispersal in a suitable liquid (e.g., water or juice), or in pre-mixed liquid form, or in solid form for oral ingestion (e.g., as solid wafers, capsules, or tablets).

The efficacy of the invention is demonstrated by clinical trials directed primarily toward measuring the effectiveness and safety as laxatives of the PEG compositions described herein. In a representative study, patients with documented constipation were evaluated for one week (the "qualification period"). If their bowel habits met the criteria for constipation, they were enrolled into the study and treated in a randomized and double-blinded fashion with 17 g of either PEG 3350 or a placebo (dextrose) for 14 days (the "treatment period"). There were 151 patients who entered the qualification phase of this study. During the qualification period, the patients maintained diaries of their bowel habits and of all symptoms experienced during both the qualification period and the treatment period. The following tables show the incidences of cramping and of gas in the patients during the qualification and the treatment periods.

TABLE 1

Qualification Period

| Qualification Period Symptom | PEG Treatment Group | Placebo Treatment Group | p value |
|---|---|---|---|
| Severe Cramping | 35.5% | 39.2% | 0.61 |
| Severe Gas | 49.5% | 60.7% | 0.13 |

Table 1 shows the percentage of patients who had symptoms of severe cramping or abdominal gas pain during the qualification period (i.e., before they received any treatment). The incidence of cramping was very comparable in the two groups of patients during the qualification period. The incidence of severe gas was somewhat higher in the group of patients who were assigned to receive the placebo.

The "chi square" statistical procedure was used to determine whether these differences were statistically significant. A 'p' value of less than 0.05 is generally accepted as indicating that an observed difference is statistically significant—i.e., that it did not occur by chance. This test revealed that the patient groups were not different from one another with regard to the incidence of the noted symptoms during the qualification period.

TABLE 2

Treatment Period

| Treatment Period Symptom | PEG Treatment Group | Placebo Treatment Group | p value |
|---|---|---|---|
| Severe Cramping | 12% | 22.6% | <0.001 |
| Severe Gas | 24% | 40.2% | <0.001 |

As shown in Table 2, however, during the treatment period the incidence of both symptoms was lower in the group treated with PEG than in the group that received the placebo; indeed, the symptom incidence in the placebo group was nearly twice that in the PEG group. This reduction in symptoms was determined to be highly statistically significant. Accordingly, PEG has been shown to reduce the incidence of cramping and gas that accompany constipation, demonstrating its effectiveness as a remedy against these symptoms. Furthermore, it is likely that PEG would also relieve the symptoms of cramping and gas in subjects who are not constipated, given the common underlying cause of these symptoms.

PEG is also found to reduce complaints of rectal irritation, which may accompany gastrointestinal distress. In particular, during the course of the treatment period, there was a statistically significant ($p=0.001$) decrease in complaints of irritation associated with PEG use.

Patient rating of irritation was scored on a five-point scale of 0 (none), 1 (mild), 2 (moderate), 3 (severe), and 4 (must discontinue). In the following table, the percentage of occurrences of each rating (0 to 4) are shown for each treatment category. The total number of observations in each category differs because the total number of bowel movements differs depending on the treatment.

TABLE 3

Patient Rating of Anorectal Irritation

| Rating | Placebo | PEG (17 g) |
|---|---|---|
| 0 (none) | 57.0% | 68.8% |
| 1 (mild) | 27.3% | 23.8% |
| 2 (moderate) | 10.7% | 7.4% |
| 3&4 (severe to discontinue) | 5.0% | 0.0% |
| Mean score | 0.6 | 0.4 |

Although the present invention has been described with reference to specific details, it is not intended that such details should be regarded as limitations upon the scope of the invention, except as and to the extent that they are included in the accompanying claims.

What is claimed is:

1. A method of ameliorating symptoms relating to at least one of (a) intestinal gas, (b) cramping and (c) anorectal irritation, the method comprising the step of administering an effective amount of a composition comprising polyethylene glycol.

2. The method of claim 1 wherein the composition is substantially free of electrolytes.

3. The method of claim 1 wherein the polyethylene glycol has an average molecular weight greater than 1000.

4. The method of claim 1 wherein the polyethylene glycol has an average molecular weight ranging from 3000 to 8000.

5. The method of claim 4 wherein the polyethylene glycol is PEG 3350.

6. The method of claim 1 wherein the composition comprises a dosage from about 5 to about 200 g of polyethylene glycol.

7. The method of claim 6 wherein the composition comprises from about 10 to about 30 g of polyethylene glycol per dose.

8. The method of claim 7 wherein the polyethylene glycol is dispersed in an aqueous medium.

9. The method of claim 7 wherein the polyethylene glycol is in solid form.

10. The method of claim 8 wherein the composition is administered up to four times per day.

11. The method of claim 1 wherein the ameliorated symptom is intestinal gas.

12. The method of claim 1 wherein the ameliorated symptom is cramping.

13. The method of claim 1 wherein the ameliorated symptom is anorectal irritation.

* * * * *